(12) United States Patent
Tanzer

(10) Patent No.: US 6,864,985 B1
(45) Date of Patent: Mar. 8, 2005

(54) MEASURING TURBIDITIES BY REFLECTOMETRY

(75) Inventor: Dieter Tanzer, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/979,055

(22) PCT Filed: May 4, 2000

(86) PCT No.: PCT/EP00/03977

§ 371 (c)(1),
(2), (4) Date: Nov. 16, 2001

(87) PCT Pub. No.: WO00/71994

PCT Pub. Date: Nov. 30, 2000

(30) Foreign Application Priority Data

May 19, 1999 (DE) .......................................... 199 22 812

(51) Int. Cl.[7] .......................... G01N 21/00; G01N 21/47
(52) U.S. Cl. ...................................... 356/446; 356/337
(58) Field of Search ................................. 356/337, 338, 356/341, 445, 446, 448

(56) References Cited

U.S. PATENT DOCUMENTS

| | | | | |
|---|---|---|---|---|
| 3,617,301 A | * | 11/1971 | Barby et al. ................. 426/442 |
| 4,263,511 A | * | 4/1981 | Hirschberg .................. 250/343 |
| 4,278,887 A | | 7/1981 | Lipshutz et al. |
| 4,320,978 A | * | 3/1982 | Sato ........................... 356/440 |
| 4,552,458 A | | 11/1985 | Lowne |
| 5,377,005 A | * | 12/1994 | Meyer ........................ 356/335 |
| 5,463,467 A | * | 10/1995 | Baumann et al. ........... 356/446 |
| 5,838,429 A | | 11/1998 | Han et al. |
| 6,124,597 A | * | 9/2000 | Shehada et al. .......... 250/461.2 |
| 6,372,485 B1 | * | 4/2002 | Clark et al. .............. 435/288.7 |
| 6,446,302 B1 | * | 9/2002 | Kasper et al. ................. 15/319 |

FOREIGN PATENT DOCUMENTS

| | | |
|---|---|---|
| EP | 0 874 233 A | 10/1998 |
| SU | 1 497 522 A | 7/1989 |

* cited by examiner

Primary Examiner—Rodney Fuller
(74) Attorney, Agent, or Firm—Millen, White, Zelano, Branigan, P.C.

(57) ABSTRACT

A method and a device for the measurement of turbidity in liquids is described, the measurement taking place by reflectometry. Reflectometers into which a cell and a diffuse reflector can be introduced are used. A method for the measurement of turbidity is described, for example for in-process controls or quality controls, which requires significantly less complex equipment than the conventional methods.

14 Claims, 4 Drawing Sheets

MEASURING TURBIDITIES BY REFLECTOMETRY

The invention relates to a method for the quantitative measurement of turbidity.

The turbidity of a liquid is caused by the presence of undissolved substances, such as, for example, suspended solid particles or emulsified oils. Turbidity measurements have manifold applications in process control/quality control in an extremely wide variety of industrial sectors, such as, for example, in food factories, water works and in the cosmetics, chemical and petrochemical industries. Turbidity measurements are particularly frequently employed for the analysis of beverages (for example measurement of the turbidity of beer and wine in breweries and wine presses) and liquids processed in industry. They are furthermore used in the analysis of aerosols and in turbidimetric titrations. In medical diagnostics, antigen or antibody assays and the concentration of other protein compounds in body fluids are determined. Turbidity measurements are furthermore employed in analytical methods using precipitation reactions.

Turbidity measurements basically serve the investigation of two different questions:

1. Does the product or the intermediate in the production process meet the desired requirements?

For example, unsatisfactory preservation, inadequate hygiene, incomplete filtration or unfavourable storage conditions of beverages may be result in the undesired multiplication of microorganisms together with turbidity. In addition, however, excessive concentrations of beverage constituents or foreign substances, such as filter aids, may also result in turbidity and change a beverage so that it becomes undrinkable. These faults can be recognised in good time with the aid of turbidity measurements.

2. How high is the concentration of a substance to be determined in the liquid to be investigated?

An example of this is the determination of potassium. Potassium ions form an insoluble precipitate with sodium tetraphenylborate in alkaline solution. The proportional correlation between the concentration of potassium and the turbidity intensity after addition of the precipitation reagent enables quantitative determination of potassium.

Besides semi-quantitative methods (methods using transparent cylinders or viewing windows), quantitative methods using optical turbidity measuring instruments are employed for determining the intensity of turbidity. Optical turbidity measuring instruments work on two different physical principles:

measurement of the attenuation of the intensity of a light beam passing through the liquid (turbidimetry)

measurement of the intensity of the scattered radiation (nephelometry)

Simple methods for analysing turbidity by means of transparent cylinders or viewing windows frequently do not meet the demands of the analytical laboratories owing to inaccuracy and subjectivity. On the other hand, only very expensive analytical instruments which can in some cases only be operated by trained personnel (photometers or pure turbidity measuring instruments, such as nephelometers) are available for quantitative determination methods based on light attenuation or light scattering. In addition, turbidity measuring instruments based on scattered-light measurement allow only determination of the turbidity of the sample alone. Frequently, however, in addition to the turbidity, it is necessary to determine further parameters in the sample, if at all possible using the same analytical instrument or analytical principle. In addition, it should be possible, especially for in-process control, to carry out the measurement directly on site using simple measuring devices.

The present invention therefore has the object of providing a method which allows simple, fast and quantitative determination of turbidity. In addition, the measurement principle should also enable the analysis of further quality-relevant parameters, likewise in a simple manner.

It has been found that quantitative turbidity measurements can be carried out in a cell using a reflectometer as is employed for the determination of support-immobilised tests and as is commercially available in a wide variety of designs. To this end, the reflectometer must be provided with a suitable cell adapter which enables the analysis of cells and with a diffuse reflector.

The invention therefore relates to a method for the measurement of turbidity in which a light beam passes through a sample, is reflected in a diffuse manner, passes through the sample again and is detected.

The invention furthermore relates to a turbidity measuring device based on a reflectometer, in which the radiation source and radiation detector are on the same side with respect to the sample.

A preferred embodiment of the measuring device according to the invention is an instrument which has light diodes as light sources and photodiodes as detectors.

Figure 2:
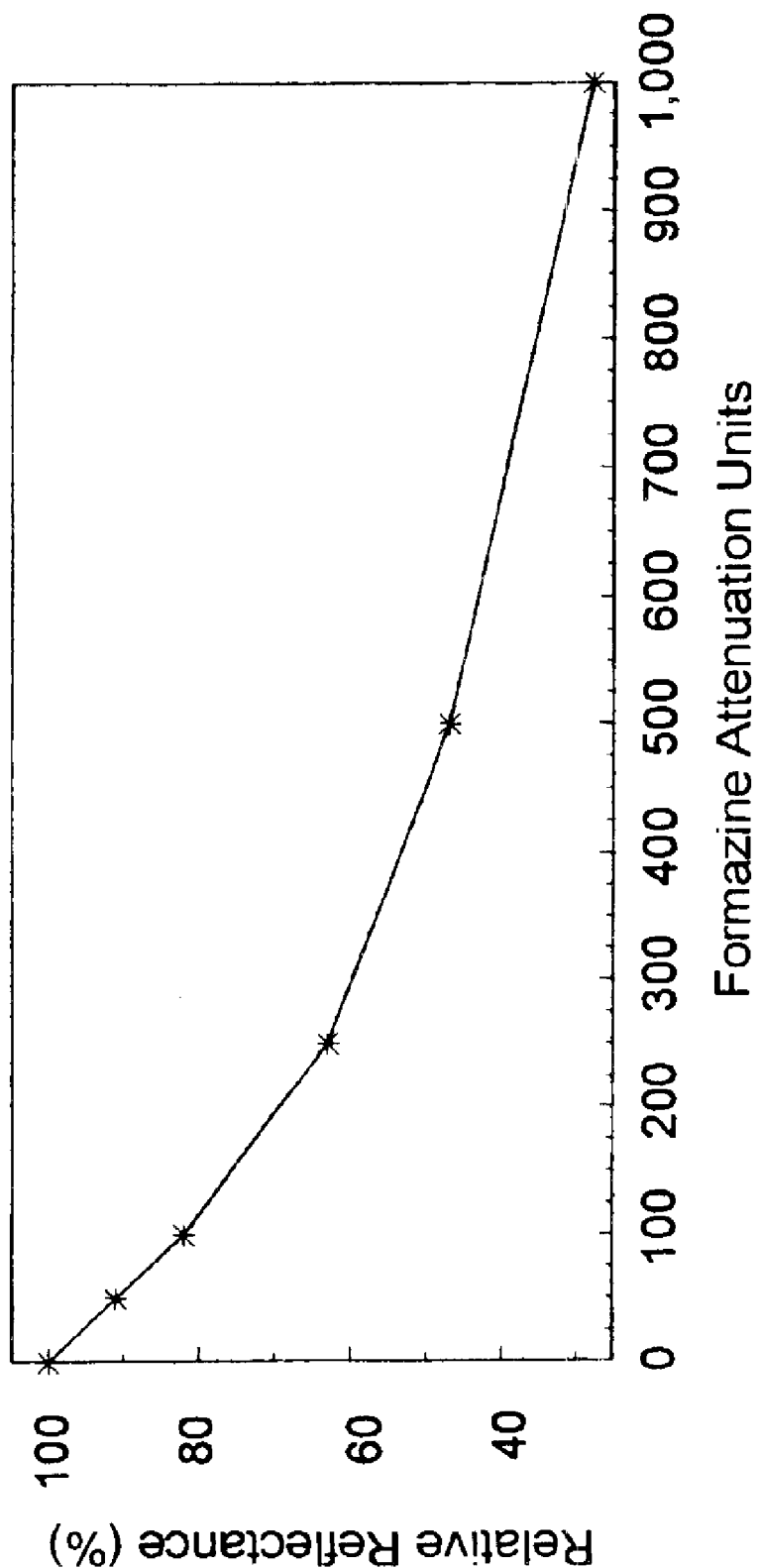
FIG. 2 shows the measurement curve of a formazine primary standard as used for calibration.
Figure 3:
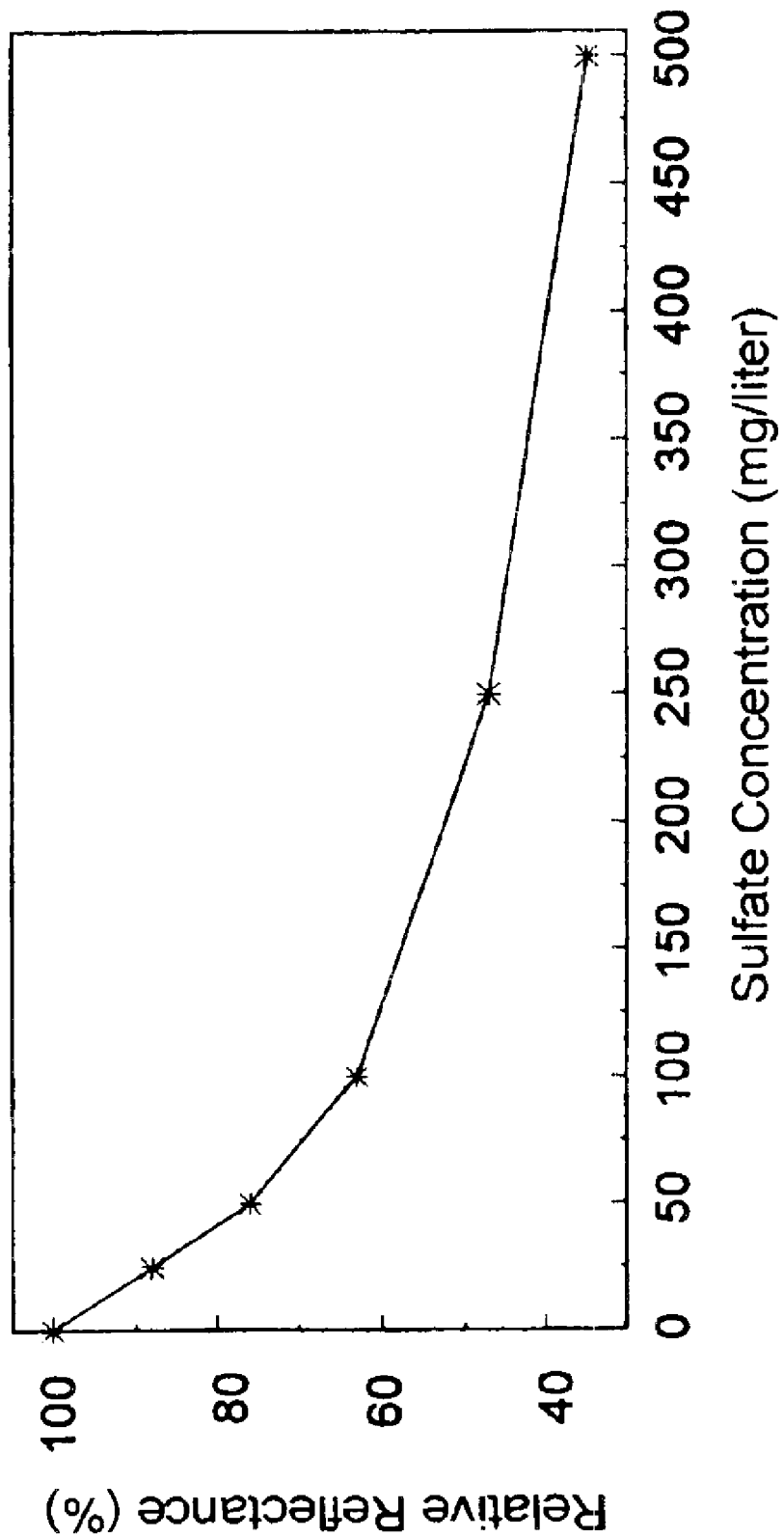
FIG. 3 shows the correlation between the concentration of sulfate and the relative reflectance obtained.
Figure 4:
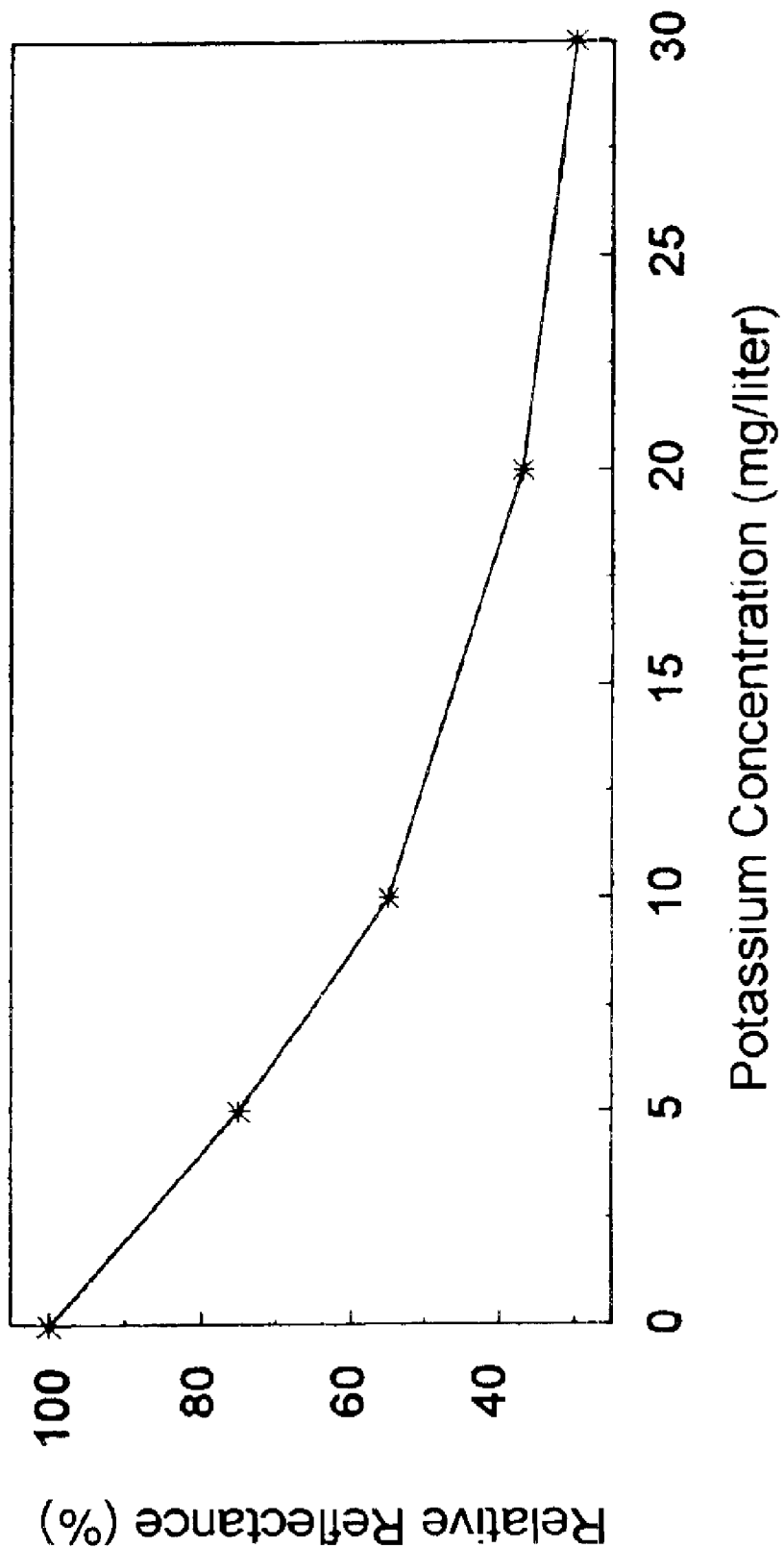
FIG. 4 shows the correlation between the concentration of potassium and the relative reflectance obtained.

Further details on FIGS. 2–4 are given in Examples 1 to 3.

In the method according to the invention, turbidity is determined by reflectometry. Reflectometry is normally employed for the evaluation of support-immobilised tests. In these tests, the reagents are embedded in corresponding layers of a solid test support, to which the sample is applied. The reaction of the sample with the reagent system results in a colour change on the test support. A variety of evaluation instruments are available for the test supports, enabling quantitative analysis of the colour change and thus of the concentration of an analyte. The evaluation instruments (reflectometers) usually operate on a reflection-photometric principle, i.e. the reflectivity (diffuse reflection) of the measurement area is measured at one or more wavelengths. Reflectometers can be made very small and inexpensive through the use of light diodes as light sources and photodiodes as detectors.

All types of reflectometers into which a cell or vessel having the same function can be introduced are suitable for the method according to the invention. These may be instruments which can simultaneously serve for evaluation of support-immobilised tests or instruments designed specifically for turbidity measurement. In both cases, a device or holder for the insertion of cells must be present. The function of diffuse reflection, which is taken on by the test strip in the case of support-immobilised tests, is taken on in the method according to the invention by a diffuse reflector, for example made of cellulose, titanium dioxide or another material known to the person skilled in the art, preferably of a suitable plastic, for example a polycarbonate, such as Makrolon®, installed behind the cell. It is equally possible to use an especially manufactured cell which has a side which reflects in a diffuse manner. These variants are referred to as diffuse reflector below.

For turbidity measurement in a reflectometer, the sample solutions are preferably introduced into a cell. These cells must have the optical properties known from transmitted-light measurement (photometry) and should have a layer thickness of 0.3–1.0 cm, more preferably 0.5 cm. They can have the usual shape for cells, i.e., for example, rectangular.

The method according to the invention can furthermore also be used for through-flow measurement. To this end, the standard cell is replaced by a through-flow cell. In this way, the turbidity of the products can be measured, for example, during production in through-flow or at defined time intervals without manual effort and replacement of the cell.

All other constituents of a reflectometer, such as light sources, detectors, mirrors, prisms or filters, are known to the person skilled in the art and can be varied in their design. Examples are given in Ullmann's Encyclopedia of Industrial Chemistry, B5, 1994. A preferred embodiment of a measuring instrument for the method according to the invention is a handy reflectometer for direct use on site, which has light diodes as light sources and photodiodes as detectors. An instrument of this type is marketed, for example, under the name RQflex Plus® by Merck KGaA, Darmstadt, Germany.

The method according to the invention can be employed for measurements as currently carried out using transparent cylinders or viewing windows or for the determination of substance concentrations in solutions.

Through the possibility of using small, easy-to-operate reflectometers, the method according to the invention offers major advantages over the conventional measurement methods using photometers or nephelometers. In addition, dry-chemical and wet-chemical tests (for example test strips, colour measurement by means of cell tests) can be carried out in addition to the reflectance measurements using the same reflectometer without the need to modify the ray path.

In the method according to the invention, a light beam, which is typically bundled due to the design of the light source, passes through the sample. The light beam is reflected in a diffuse manner after passing through the sample and passes through the sample again. Detection is finally effected at an angle to the direction of incidence of the beam. This angle between the incident beam and the detector should not be in the region of the regular reflection. In the method according to the invention, the light beam can hit the sample and the diffuse reflector perpendicularly or at an angle of between 90 and 30°. In this case, the angle of the detector is adapted correspondingly. Perpendicular incidence, i.e. at an angle of 90°, to the sample is preferred, with detection at a corresponding angle thereto.

However, the scattered light is not, as in nephelometry, measured at an angle, for example perpendicular to the direction of incidence. Instead, the attenuation of the light beam caused by the turbidity of the solution is determined. The attenuation of the light beam as a parameter of the strength of the turbidity is also used in known turbidimetric methods. However, the light source and detector are on opposite sides of the sample in photometric methods, whereas in the measurement according to the invention the light beam passes through the sample, is reflected in a diffuse manner and passes through the sample again. The light source and detector are accordingly on the same side of the measurement cell or sample. The working range in the method according to the invention is therefore selected in such a way that the turbidity in the sample results merely in light attenuation. In the case of excessively strong turbidity, an excessive signal which is not modified by sample parameters is observed.

The accuracy of the determination of small amounts of dissolved substances by turbidity measurement, for example after precipitation reactions, is dependent on the production of suitable standards for the calibration, since the particle size of a precipitate is dependent on many factors (temperature, pH, foreign electrolytes, etc.). The turbidity is therefore a convention parameter. For calibration of the turbidity measuring instruments according to the invention, aqueous solutions of formazine, which can be obtained from a reaction of hydrazine sulfate and hexamethylenetetra-amine, are used as turbidity standard, as usual in conventional methods. In order to distinguish the measurement method used, the turbidity units defined are "formazine attenuation units" (FAU) in the case of measurement of the intensity of the light attenuation and "formazine nephelometric units" (FNU) in the case of the measurement of the intensity of the light scattering. Accordingly, the reflectometers employed for the method according to the invention are preferably calibrated in "formazine attentuation units" (FAU).

The instruments are preferably likewise pre-calibrated for the quantitative determination of other substances. To this end, a calibration curve is recorded as described, for example, in Example 3. The correlation between the concentration of analyte and relative reflectance (calibration curve) obtained during the calibration measurement is then encoded on a bar code, preferably by means of common mathematical functions (for example cubic spline function), so that, on measurement of samples, the relative reflectance values measured are converted directly into corresponding concentration units, which can be read off the display of the reflectometer.

Details of turbidity measurement are dealt with in the following standards: EN 27027, ISO 7027, US Standard APHA 2120 B.

Furthermore, all instruments employed for the method according to the invention must firstly be pre-calibrated with a standard, for example with a standard solution, the standard preferably absorbing uniformly over the entire wavelength range. All instruments consequently exhibit a uniform measurement signal relative to this standard solution, so that comparative measurements can also be carried out independently of the instrument.

The instruments according to the invention differ from all known reflectometers through the special pre-calibration and calibration with standards for turbidity measurement. Through their calibration, they can be matched to the particular need and measurement problem.

Figure 1:
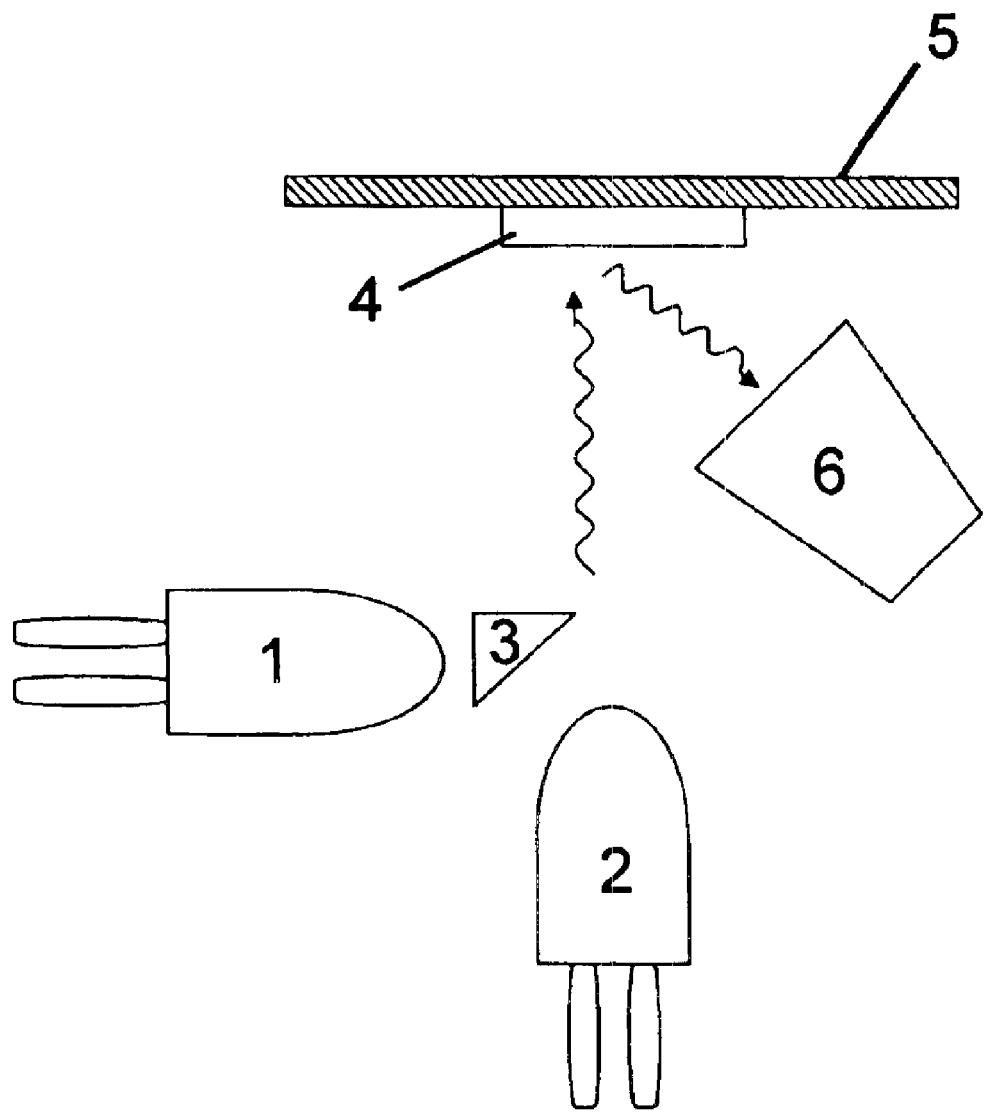
FIG. 1 shows a corresponding embodiment of a turbidity measuring instrument according to the invention.

FIG. 1 shows a diagrammatic view of a typical design of a measurement device according to the invention. The light diodes 1 and 2 serve as light source. They enable the incidence of various wavelengths. Furthermore, various angles of incidence can be achieved by means of prisms or mirrors (3). The beam hits the sample cell (4) and passes through it. In the process, some of the beam is scattered and attenuated by the medium. After passing through the sample, the beam is reflected in a diffuse manner at the reverse side by a diffuse reflector (5). After passing through the sample again, the light attenuation is measured at an angle to the direction of incidence using a photodiode (6). The radiation source (1, 2) and detector (6) are located on the same side of the cell.

Even without further details, it is assumed that a person skilled in the art will be able to utilise the above description in its broadest scope. The preferred embodiments and examples should therefore merely be regarded as descriptive disclosure, in no sense as limiting in any way.

The complete disclosure content of all applications, patents and publications mentioned above and below and of the corresponding application DE 199 22 812, filed on 19.05.1999, is incorporated into this application by way of reference.

EXAMPLES

1. Analysis of Turbidity Standards

Formazine primary standards, as employed for the calibration of turbidity measuring instruments, were measured in Makrolon® cells having a layer thickness of 0.6 mm using a reflectometer according to the invention. The reflectance values were in each case determined at 660 nm relative to distilled water as blank value. The results are shown graphically in FIG. 2. The relative reflectance is plotted on the ordinate, and the formazine attentuation units (FAU) are plotted on the abscissa.

2. Determination of the Concentration of Sulfate by Turbidity Measurement 0.25 ml of a solution of barium chloride hydrate in demineralised water (10 g of $BaCl_2 \times 2H_2O$ in 90 ml of water) was added to 5 ml of aqueous sulfate standard solution. The samples were measured as described in Example 1.

The correlation between the concentration of sulfate and the relative reflectance values obtained is shown graphically in FIG. 3. The relative reflectance (ordinate) was plotted against the concentration of sulfate in mg/l (abscissa).

3. Determination of the Concentration of Potassium by Turbidity Measurement

Performance of the Calibration:

Potassium standard solutions were rendered alkaline (pH 10.7) using sodium hydroxide solution. 0.3 ml of formaldehyde solution (37%) and, by means of a microspoon, about 100 mg of sodium tetraphenylborate were then added successively to each 5 ml sample. The samples were measured as described in Example 1.

The correlation between the concentration of potassium and the relative reflectance values obtained is shown graphically in FIG. 4. To this end, the relative reflectance (ordinate) was plotted against the concentration of potassium in mg/l (abscissa).

Variance Comparison:

The correlation obtained in Example 3 between the concentration of potassium and the relative reflectance (calibration curve) was encoded on a bar code by means of a common mathematical function (cubic spline function), so that on measurement of samples, the relative reflectance values measured are converted directly into corresponding concentration units, which can be read off the display of the reflectometer. Various potassium standards were subsequently measured. In this variance comparison, the following results were obtained:

| Theoretical [mg/l of potassium] | Actual [mg/l of potassium] |
|---|---|
| 0.5 | 0.5 ± 0.1 |
| 2.5 | 2.5 ± 0.1 |
| 10.0 | 10.2 ± 0.5 |
| 25.0 | 25.9 ± 0.9 |

4. Analysis of Soil Samples

Soil samples were extracted with DL solution in accordance with the LUFA standard (Verband Deutscher Landwirtschaftlicher Untersuchungs-u. Forschungsanstalten, Methodenhandbuch [Methods Manual], Volume 1, The Analysis of Soils, 4th Edition 1991; Chapter A 6.2.1.2) and treated as described under Performance of the Calibration. The samples obtained were subsequently measured in the reflectometer. For comparison, the samples were analysed by atomic absorption spectrometry (AAS). The results obtained are shown below.

| Sample | Turbidity measurement | AAS |
|---|---|---|
| 1 | 4.6 | 4.8 |
| 2 | 5.2 | 5.1 |
| 3 | 21.8 | 23.4 |

[The potassium contents are indicated in mg/l of extraction solution]

What is claimed is:

1. A method for measuring the turbidity of a liquid sample by reflectometry, which comprises:

passing a light beam through the liquid sample to a diffuse reflector which reflects the light in a diffuse manner back through the sample again and measuring the intensity of the light reflected in a diffuse manner and attenuated by the turbidity of the sample to determine the turbidity of the liquid.

2. The method of claim 1, wherein the light beam source and a detector for measuring the intensity of the light reflected in a diffuse manner and attenuated by the turbidity of the sample are located on one side of the sample and the diffuse reflector is located on the opposing side of the sample.

3. The method of claim 2, wherein the light beam source is at least one light diode and the detector is as least one photodiode.

4. The method of claim 1, wherein the liquid sample is provided by a cell containing the liquid which has a thickness in the direction between the light beam source and the diffuse reflector of 0.3 to 1.0 cm.

5. The method of claim 4, wherein the cell is a through-flow cell wherein the liquid sample is flowed continuously therethrough.

6. The method of claim 1, wherein the measuring of the intensity of the light reflected in a diffuse manner and attenuated by the turbidity of the sample is by a detector arranged at an angle to the direction of incidence of the light beam, which angle is not in the region of regular reflection.

7. The method of claim 1, wherein the light beam is provided through the sample at an angle perpendicular to the diffuse reflector.

8. A turbidity measuring device for measuring the turbidity of a liquid sample by reflectometry in accordance with claim 1, which comprises a means for holding a liquid sample to be measured, a light beam source for passing a light beam through the liquid sample, a diffuse reflector for reflecting light passed through the sample in a diffuse manner back through the sample again and a detector for measuring the intensity of the light reflected in a diffuse manner and attenuated by the turbidity of the sample.

9. The device of claim 8, wherein the light beam source and the detector are located on one side of the means for holding the liquid sample and the diffuse reflector is located on the opposing side of the means for holding the liquid sample.

10. The device of claim 9, wherein the light beam source is at least one light diode and the detector is at least one photodiode.

11. The device of claim 8, wherein means for holding the liquid sample is a cell for containing the liquid which has a thickness in the direction between the light beam source and the diffuse reflector of 0.3 to 1.0 cm.

12. The device of claim 11, wherein the cell is a through-flow cell which allows for the liquid sample to be flowed continuously therethrough.

13. The device of claim 8, wherein the detector is arranged at an angle to the direction of incidence of the light beam, which angle is not in the region of regular reflection.

14. The device of claim 8, wherein the light beam is provided through the sample at an angle perpendicular to the diffuse reflector.

* * * * *